(12) United States Patent
Mano et al.

(10) Patent No.: US 6,225,459 B1
(45) Date of Patent: May 1, 2001

(54) TEC PROMOTER

(75) Inventors: Hiroyuki Mano, Tochigi; Tsuneaki Sakata, Osaka; Mamoru Hasegawa, Ibaraki, all of (JP)

(73) Assignee: Dnavec Research Inc., Tsukuba (JP)

( * ) Notice: Subject to any disclaimer, the term of this patent is extended or adjusted under 35 U.S.C. 154(b) by 0 days.

(21) Appl. No.: 09/142,529

(22) PCT Filed: Mar. 12, 1997

(86) PCT No.: PCT/JP97/00741

§ 371 Date: Aug. 12, 1999

§ 102(e) Date: Aug. 12, 1999

(87) PCT Pub. No.: WO97/34007

PCT Pub. Date: Sep. 18, 1997

(30) Foreign Application Priority Data

Mar. 12, 1996 (JP) .................................................. 8-54294

(51) Int. Cl.⁷ .................................................. C07H 21/04
(52) U.S. Cl. .................. 536/24.1; 536/23.1; 435/320.1; 435/325
(58) Field of Search ................. 536/23.1, 24.1; 436/320.1, 325

(56) References Cited

PUBLICATIONS

Mano, et al. Oncogene 8: 417–424, 1993.*
Dzerzak et al., "Lineage–specific expression of a human β–globin gene in murine bone marrow transplant recipients reconstituted with retrovirus–transduced stem cells" *Nature* 331:35–41 (1988).
Ido et al., "Gene therapy for hempatoma cells using a retrovirus vector carrying herpes simplex virus thymidine kinase gene under the control of human α–fetoprotein gene promoter" *Cancer Research* 55:3105–3109 (1995).
Mano et al., "A novel protein–tyrosine kinase, tec, is preferentially expressed in liver" *Oncogene* 5:1781–1786 (1990).
Mano et al., "Expression of a novel form of Tec kinase in hematopoietic cells and mapping of the gene to chromosome 5 near Kit" *Oncogene* 8:417–424 (1993).

* cited by examiner

Primary Examiner—David Guzo
Assistant Examiner—Gerald G. Leffers
(74) Attorney, Agent, or Firm—Clark & Elbing LLP

(57) ABSTRACT

The present invention provides a DNA having promoter activity of Tec tyrosine kinase and a vector having incorporated within it the promoter to thereby enable a high level expression of an exogenous gene in hematopoietic stem cells and hepatic cells.

4 Claims, 2 Drawing Sheets

Fig. 1

```
AGCTTGTCAG TAAGCCACCA TTCTTCTATC ACCCCAGAGC ACAGCATCAT CGGTTTTCAC   60
CCGCGAGGGG CTAAGCGGAA GTGGAGGTCG GTTCTTAGCC ACCCACAAGT GCTATTGCTA  120
CGTCCTCCGA GCCGGGGATC GAAGGAGCAT TTTTCTGGAC GGTTCTCTTA GGATGGGAAG  180
TCCGGACTTA GAGAGACCCC ACGCCCGCGT CTGTCTGGATA AGAGACCCTC CCTGGAACTT  240
                                      GATA
CGGCCCGCAG ACCGAGAGCT CCGATTCTTC CCTTTGGCTT TGAAATCGCG GAAGGAAGGT  300
GGGACACTGG CGCTCTGGGC ACGAGGCAGA GCGACGCGGA GGCGGGCCAG GAGAGCCGGG  360
                                                   SP-1
CGGTGGGCGT GGCGATGGGT TTGGTCAGCG CTTGCCCAGC TCCGGGCCTC GCAGTTTGGA  420
                                                SP-1
CGTCGCTCTG TCTTGGCTTG TCTCGGCACG CGCTCCGCCG CGCTCCGTCA AGGTAAGAAC  480
                                                        CAAGGGACTC
```

TEC PROMOTER

TECHNICAL FIELD

The present invention relates to the field of genetic engineering, particularly the field of gene therapy.

BACKGROUND ART

Gene therapy attempts to treat diseases caused by congenital or acquired genetic defects, namely gene disorders, by substituting or supplementing defective genes with normal genes. Although various treatment methods for gene therapy have been investigated, only a very limited number of the methods to date have met with success, including the treatment of adenosine deaminase (ADA) deficiency. This is mainly because the methods for efficiently introducing a therapeutic gene into target cells and the methods for expressing an introduced gene in the cell have not yet been established. So far, liposomes, HVJ-liposomes, retroviruses, and the like have been employed as carriers introducing the therapeutic gene into target cells. However, none of them are satisfactory in gene introduction efficiency. Various attempts have been made to increase the expression efficiency of the introduced gene, by, for example, improving the promoter. However, in each case the expression efficiency of the desired gene was still poor, and the quantity of the gene product was insufficient to afford gene therapy. Thus, in the field of gene therapy, a vector that enables a high level expression of a therapeutic gene in a variety of target cells has been sought.

In the field of hematology, Tec tyrosine kinase, a protein thought to participate in the proliferation of hematopoietic stem cells, is highly expressed in mouse liver, and is also expressed in the kidney, heart, and ovary (Oncogene, 5, 1781–1786 (1990)). In humans, Tec tyrosine kinase is highly expressed in a wide range of blood and lymphoid cells (LEUKEMIA, 8, 1663–1672 (1994)).

DISCLOSURE OF THE INVENTION

An objective of the present invention is to provide a vector having incorporated within it a promoter functioning efficiently in a wide variety of blood and lymphoid cells, and the cells of organs such as the liver, thereby providing a gene therapy technique targeting blood and lymphoid cells.

The present inventors noted that Tec tyrosine kinase, a protein thought to participate in the proliferation of hematopoietic stem cells, is highly expressed in a wide variety of blood cells, lymphoid cells, and the cells of organs such as the liver. The inventors isolated the promoter of Tec tyrosine kinase from a mouse genomic DNA, constructed a vector with the promoter incorporated within it ligated an exogenous gene adjacently downstream of it, and attempted to express the exogenous gene in the cells. As a result, they found that the exogenous gene was actually expressed in the cells at a high level, thereby completing the present invention. Thus, the present invention relates to:

(1) a DNA comprising at least a part of the nucleotide sequence of SEQ ID No:1 and having promoter activity;

(2) an expression vector comprising the DNA of (1); and (3) a cell carrying the expression vector of (2).

In the present invention, "a DNA having promoter activity" means a DNA having activity to induce the transcription of a DNA region adjacent to the DNA. The present invention includes a DNA containing a part of the nucleotide sequence of SEQ ID No:1, and having promoter activity as well as the DNA having the nucleotide sequence of SEQ ID No:1. Preferably, the DNA of the present invention has a general length of at least about 50 bp, more preferably at least about 100 bp, even more preferably at least about 200 bp, and most preferably at least about 300 bp.

According to the present invention, any vector for use in gene introduction can basically be used as a "vector" into which the DNA having promoter activity is to be introduced. Particularly in gene therapy, viral vectors, such as retrovirus vectors, adenovirus vectors, or adeno associated virus vectors, and non-viral vectors such as liposomes should be used.

Any cell is included in the "cell carrying the expression vector" of the present invention. Cells that have been confirmed to actually express the Tec tyrosine kinase gene, including blood cells and lymphoid cells, such as hematopoietic stem cells, myeloid cells, B cells, and T cells, and the cells of internal organs such as the liver, kidney, heart, and ovary should be used.

BRIEF DESCRIPTION OF THE DRAWINGS

FIG. 1 shows the nucleotide sequence of the 5' flanking region of a mouse Tec gene according to the present invention (SEQ. I.D. No.: 1).

BEST MODE FOR IMPLEMENTING THE INVENTION

Figure 2:
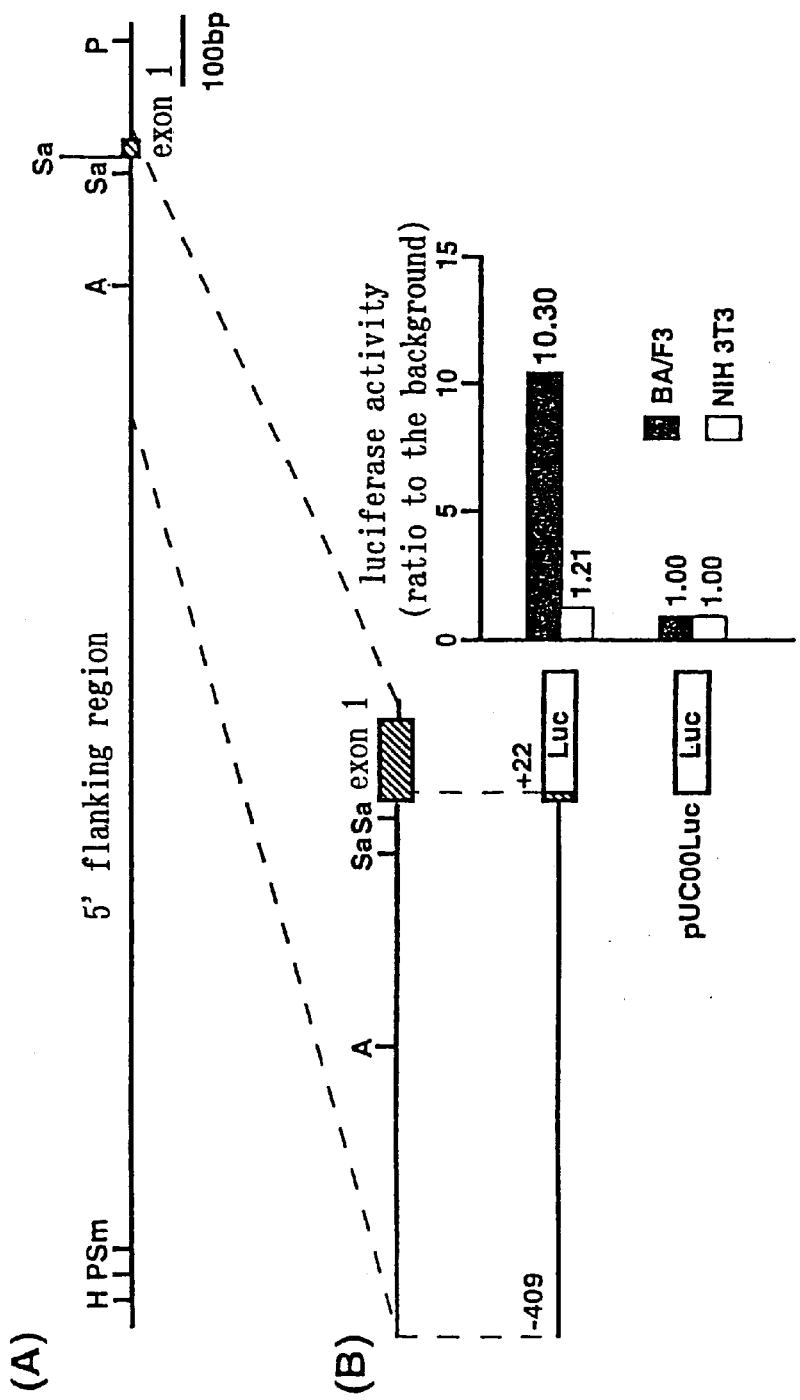
FIG. 2 shows the luciferase activity of BA/F3 and NIH 3T3 cells, into which pUC00Luc, having incorporated within it a 5' flanking region fragment of a mouse Tec gene and a luciferase gene adjacently linked thereto, was introduced. As a control pUC00Luc, which does not contain a 5' flanking region fragment, was used.

The following examples will be given to illustrate the present invention in detail, but are not construed to limit the scope of the present invention.

EXAMPLE 1

Construction of the mouse genomic library

A high molecular weight genomic DNA was extracted from BA/F3 cells. The DNA was partially digested with Sau3AI (Takara Shuzo), and dephosphorylated with bacterial alkaline phosphatase (BAP; Takara Shuzo). The resulting DNA fragments were incorporated into the BamHI-digested EMBL3 vector (Stratagene), and in vitro packaged using "Gigapack Gold extracts" (Stratagene). The recombinant phage thus obtained was used to infect the E. coli LE392 strain.

EXAMPLE 2

Screening of the mouse Tec promoter

In order to obtain the promoter region from a mouse Tec gene, a screening probe was prepared by PCR as follows. First, a primer corresponding to the 15th through the 32nd nucleotides, and a primer corresponding to the 122nd through the 141st nucleotides of the Tec cDNA (SEQ ID No:2; Oncogene, 8, 417–424 (1993)) were synthesized, and used to amplify the 5' region of the mouse Tec cDNA. The amplification by PCR was performed using 10 ng of the mouse Tec cDNA as a template. The PCR product (approximately 127 bp) was thus purified, radioactively labeled with $^{32}p$, and used as a probe to screen the mouse genomic library by performing hybridization in a solution containing 5×SSC (1×SSC: 150 mM NaCl, 15 mM Na-Citrate), 5×Denhardt's solution (1 mg/ml polyvinylpyrrolidone, 1 mg/ml bovine serum albumin, 1 mg/ml Ficoll), 0.5% SDS, 100 ng/ml salmon sperm DNA, and the $^{32}$P-labeled PCR fragment, at 65° C. overnight. The filters were washed twice in 2×SSC/0.1% SDS at 55° C. for 20 minutes, and twice in 0.2×SSC/0.1% SDS at 55° C. for 20 minutes. The signal was detected by exposing the filters onto "Kodak XAR Films" (Kodak) with intensifying screens for 24 to 72 hours at −80° C. As a result, 13 positive clones were obtained. The secondary screening was done for these positive clones using as a probe the nucleotide corresponding to the Tec cDNA positions 15 to 39 that was radioactively labeled in the same manner as above by performing hybridization under the same conditions as above except that the temperature was 55° C., and the washing was done twice in 2×SSC/0.1% SDS at 55° C. for 20 minutes each time. Consequently, two positive clones were obtained.

EXAMPLE 3

Analysis of the transcription initiation site of the mouse Tec gene

In order to analyze the transcription initiation site of the mouse Tec gene, RACE-PCR was performed as follows. First, 5 µg of mRNA was extracted from BA/F3 cells and annealing was performed using the oligonucleotide, 5'-TTAGCATCATGAACAAC-3' (Primer 1) SEQ ID NO:3, which corresponds to the nucleotide positions 358 through 374 of the Tec cDNA (hereinafter applying the same nucleotide positions as in SEQ ID NO:2) as an antisense primer against this mRNA. The annealing product was subjected to cDNA synthesis and d(A) tailing. The primary PCR was then performed using the above primer as the template and using as primers the oligonucleotide, 5'-CCTTACCCTCATAGTAGCTCA-3' (Primer 2) SEQ ID NO:4, which corresponds to the nucleotide positions 227 through 247 of the Tec cDNA, and the oligonucleotide, 5'-GACTCGAGTCGACATCGATTTTTTTTTTTTTTTTT-3' (Primer 3) SEQ ID NO:5. The primary PCR was done for 40 cycles of 94° C. for 40 sec, 55° C. for 2 min, and 72° C. for 3 min. In addition, the secondary PCR was performed under the same conditions as the primary PCR, except that the oligonucleotide, 5'-TCAACACTATCCTAGAAGAG-3' (Primer 4) SEQ ID NO:6, which corresponds to the nucleotide positions 122 through 141 of the Tec cDNA, and the oligonucleotide, 5'-GACTCGAGTCGACATCG-3, Primer 5; SEQ ID NO:7 were used instead of Primer 2 and Primer 3. As a negative control for this experiment, a RACE-PCR was done without the reverse transcriptase. Next, the PCR products were electrophoresed on agarose, and stained with ethidium bromide (EtBr). As a result, a PCR product of approximately 250 bp was detected only when the RACE-PCR was performed with the reverse transcriptase. In order to confirm that the desired region had been amplified, the PCR products were transferred onto a nitrocellulose membrane after the agarose electrophoresis was hybridizated against this membrane using the $^{32}$P-labeled oligonucleotide, 5'-GCAGTTTGGACGTCGCTCTGTCTTG-3', SEQ ID NO:8 which corresponds to the nucleotide positions 15 through 39 of the Tec cDNA. The result showed that the PCR products contained most of the 5' region of the Tec cDNA, and that the Tec mRNA was accurately amplified by RACE-PCR.

When the 5'-side sequences of the thus-obtained DNA fragments were determined, an identical sequence (5'-CGCAGTTTGG . . . ) (SEQ ID NO:1) after polyT sequence was found in seven out of eight clones, and therefore, the 5' terminal "C" of the sequence was identified as the transcription initiation site. The transcription initiation site is indicated by arrows in FIG. 1.

EXAMPLE 4

Analysis of the 5' flanking region of the mouse Tec gene

The nucleotide sequence of the 5' flanking region of the mouse Tec gene was determined by the dideoxy method. The sequence thus determined is shown in FIG. 1, and SEQ ID No:1. The result indicated that there is no sequence, which is clearly identified as a TATA box or a CAAT box within the 5' flanking region. Instead, there was a GATA site and a consensus sequence for the SP-1 factor-binding site (FIG. 1).

EXAMPLE 5

Analysis of promoter activity of the 5' flanking region of the mouse Tec gene

A fragment consisting of a part of the mouse Tec gene 5' flanking region and exon 1 (the region from −409 to +22) was incorporated into an expression vector containing no promoter, pUC00Luc, and introduced into BA/F3 cells, which highly express the Tec mRNA, and into NIH 3T3 cells, which do not express the Tec mRNA, as follows. First, 1 ×10$^7$ cells in their growth phase were washed with PBS, and incubated with 500 µg of DEAE dextran (Pharmacia) and 10 µg of a reporter plasmid DNA at room temperature for 25 minutes. The cells were then cultured in the medium containing 100 µM chloroquine at 37° C. for 1 hour. The culturing was done in 5% carbon dioxide. The cells were washed with PBS, incubated in the culture medium for 48 hours, and harvested for the luciferase analysis using the "Luciferase Assay System" (Promega). As a control in the above experiment, the cells into which pUC00Luc containing no 5' region fragment had been introduced were used. The luciferase activity assay was performed according to the ordinary method (the method according to the manual of "Luciferase Assay System" (Promega)).

From the results obtained, BA/F3 cells showed 10 times higher luciferase activity than NIH 3T3 cells when pUC00Luc containing the 5' region fragment was introduced into these cells (FIG. 2). In contrast, in the control experiment, no luciferase activity was detected in any cell line (FIG. 2). Consequently, it was revealed that the 5' flanking region of the mouse Tec gene possesses promoter activity.

It is acknowledged that one skilled in the art may be able to prepare and identify a shorter DNA fragment by preparing a shorter promoter having nucleotide sequence of SEQ ID No:1 by digestion with exonucleases such as ExoIII and Bal31 or restriction enzymes and examining the promoter activity of the DNA fragments according to the method described in this Example.

INDUSTRIAL APPLICABILITY

In the present invention, the promoter of the Tec tyrosine kinase, which is highly expressed in a wide variety of blood cells, lymphoid cells, and the cells of organs such as the liver, was isolated, and its structure was clarified. Furthermore, the present invention enables the production of a vector having incorporated within it the promoter and a high level expression of an exogenous gene in hematopoietic stem cells, and the like. A major breakthrough is expected particularly in the field of gene therapy targeting blood cells or the cell of organs such as the liver.

What is claimed is:

1. A recombinant DNA having promoter activity consisting essentially of SEQ ID NO: 1 wherein the promoter activity is associated with SEQ ID NO: 1.

2. A recombinant DNA having promoter activity consisting essentially of nucleotides 1–431 of SEQ ID NO: 1 wherein the promoter activity is associated with nucleotides 1–431 of SEQ ID NO: 1.

3. An expression vector comprising the recombinant DNA of claim 1 or 2.

4. A cell comprising the expression vector of claim 3.

* * * * *

UNITED STATES PATENT AND TRADEMARK OFFICE
CERTIFICATE OF CORRECTION

PATENT NO.     : 6,225,459 B1
DATED          : May 1, 2001
INVENTOR(S)    : Hiroyuki Mano, Tsuneaki Sakata and Mamoru Hasegawa It is certified that error appears in the above-identified patent and that said Letters Patent is hereby corrected as shown below:

Title page,
Item [54], replace "TEC PROMOTER" with -- PROMOTER --;
Item [73], replace "Tsukuba" with -- Ibaraki --;
Item [22], replace "March 12, 1997" with -- March 10, 1997 --;
Item [56], PUBLICATIONS, replace "Dzerzak et al." with -- Dzierzak et al. --; replace "hempatoma" with -- hepatoma --; insert -- Honda et al., "Cloning and Characterization of Mouse *tec* Promoter," *Biochemical and Biophysical Research Communications* 223:422-426 (1996). --;

Column 2,
Line 24, replace "(SEQ. I.D. No.: 1)" with -- (SEQ ID NO:1) --;
Line 66, replace "$^{32}$p" with -- $^{32}$P --;

Column 3,
Line 5, replace "65° C." with -- 65°C --;
Lines 6, 7, 16, 17 and 41, replace "55° C." with -- 55°C --;
Line 41, replace "94° C." with -- 94°C --;
Line 41, replace "72° C." with -- 72°C --;

Column 4,
Line 34, replace "37° C." with -- 37°C --;

UNITED STATES PATENT AND TRADEMARK OFFICE
CERTIFICATE OF CORRECTION

PATENT NO.   : 6,225,459 B1
DATED        : May 1, 2001
INVENTOR(S)  : Hiroyuki Mano, Tsuneaki Sakata and Mamoru Hasegawa It is certified that error appears in the above-identified patent and that said Letters Patent is hereby corrected as shown below:

Column 5,
Line 2, replace "stem cells, and the like" with
-- stem cells, liver cells, and the like --; and Column 6,
Line 2, replace "cell" with -- cells --.

Signed and Sealed this

Eleventh Day of February, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 480
<212> TYPE: DNA
<213> ORGANISM: Mus musculus

<400> SEQUENCE: 1

```
agcttgtcag taagccacca ttcttctatc accccagagc acagcatcat cggttttcac      60
ccgcgagggg ctaagcggaa gtggaggtcg gttcttagcc acccacaagt gctattgcta     120
cgtcctccga gccggggatc gaaggagcat ttttctggac ggttctctta ggatgggaag     180
tccggactta gagagacccc acgccgcgtc tgtctggata agagacgctc cctggaactt     240
cggccgcagg accgagagct ccgattcttc cctttggctt tgaaatcgcg gaaggaaggt     300
gggacactgg cgctctgggc acgaggcaga gcgacgcgag gcgggccag gagagccggg      360
cggtgggcgt ggcgatgggt ttggtcagcg cttgccgagc tccgggctcc gcagtttgga     420
cgtcgctctg tcttggcttg tctcggcacg cgctccgtca aggtaagaac caagggactc     480
```

<210> SEQ ID NO 2
<211> LENGTH: 2574
<212> TYPE: DNA
<213> ORGANISM: Mus musculus

<400> SEQUENCE: 2

```
gagctccggc ctccgcagtt tggacgtcgc tctgtcttgg cttgtctcgg cacgcgctcc      60
gtcaagaatc cggagatcgt caatggctgg agaaagagca accagaagac cgagatgaat     120
ttcaacacta tcctagaaga gattcttatt aaaaggtccc agcagaaaaa gaagacatca     180
ctcttaaact acaaagagag actttgtgta cttccaaaat ccgtgttgag ctactatgag     240
ggtcgagcgg agaagaaata cagaaagggc gtcattgata tttccaaaat caagtgtgtg     300
gagatagtga agaacgatga tggtgtcatt ccctgtcaaa ataaatttcc attccaggtt     360
gttcatgatg ctaatacact ttatattttt gcacctagtc cacaaagcag ggaccgatgg     420
gtgaagaagt taaagaaga aataaagaac aacaataata tcatgattaa ataccatcct     480
aaattctggg cagatgggag ttaccagtgt tgtagacaaa cagaaaaact agcacccgga     540
tgtgagaagt acaatctttt tgagagtagt ataagaaaga ccctgcctcc cgcgccagaa     600
ataaagaaga gaaggcctcc tccaccaatt cccccagagg aagaaaatac tgaagaaatc     660
gttgtagcga tgtatgactt ccaagcgacg gaagcacatg acctcaggtt agagagaggc     720
caagagtata tcatcctgga aaagaatgac ctccattggt ggagagcgag agataagtat     780
gggagtgaag gatatatccc aagtaattac gtcacaggga agaaatccaa caacttagat     840
caatatgagt ggtactgcag aaataccaac agaagcaaag cagaacagct cctcagaacg     900
gaagataaag aaggtggttt tatggtgaga gactccagtc aaccaggctt gtacactgtc     960
tccctttaca caaagtttgg gggagaaggc tcatcaggtt tcaggcatta tcacataaag    1020
gaaacagcaa catcccaaa gaagtattac ctggcagaga agcatgcttt cggtccatt     1080
cctgagatca ttgaatatca aagcacaat gcggcaggc ttgtcaccag gctgcggtac    1140
ccggtcagta caagggggaa gaacgctccc actactgcgg ccttcagcta tgataagtgg    1200
```

```
gagattaacc catcagagct gacctttatg agagagttgg ggagcggact gtttggagtg    1260
gtgaggcttg gcaagtggcg ggcccagtac aaagtggcca tcaaagctat ccgggaaggc    1320
gccatgtgtg aagaggattt catagaggaa gctaaagtca tgatgaagct gacacacccc    1380
aagctggtac agctctatgg tgtatgcacc cagcagaagc ccatctacat cgttaccgag    1440
ttcatggaac ggggctgcct tctgaatttc ctccggcaga gacaaggcca tttcagcaga    1500
gacatgctgc taagcatgtg tcaagatgtc tgtgaaggga tggagtacct ggagagaaac    1560
ttcttcatcc acagagacct ggctgccaga aattgtctag tgaatgaagc aggagttgtc    1620
aaagtatctg attttggaat ggccaggtac gttctggatg atcagtacac aagttcttct    1680
tgcgccaagt tccctgtgaa gtggtgtccc ccagaagtgt ttaattacag ccgctttagc    1740
agcaagtcag acgtctggtc gtttggtgtg ctaatgtggg aaatattcac agaaggcagg    1800
atgccctttg agaagaacac caattacgaa gtggtaacca tggtgactcg tggccaccgc    1860
ctccaccggc caaagctggc ttccaaatat ttgtatgagg tgatgctgag atgctggcaa    1920
gagagaccaa agggaaggcc ttcctttgaa gacttgctgc gtacgataga tgaactagtt    1980
gaatgtgaag aaacttttgg aagatgaatg gtggtcccag tttccaaggc aagaggaaga    2040
aatggtgtgc catcggaacg caattctctt ggcacctggg agtatagact gctctgctta    2100
caacacggta gccccagctc atctgctgct gatccagcct gagctcagtc cctgctttgc    2160
cggctgcaca gatggtctct cagagctggt gacgtgaagc actgattttg ctcatttctt    2220
caagggtttg agtgccagcc atgtatacca ggctctgtgc ccaggcctca ggagatgaac    2280
atgggactat gctagctgat gctagcggaa agccagggtg gttgtgatgg ggacgagtca    2340
tgtcccagcg tctcttccat gcccttggc tattacataa acctgggcct ggagtgttgt    2400
ctaccactga gttctaggaa aagcaggaac ccacctggat acgtagtaat cctctgtttt    2460
ggaaacatct ctttccaaac ttgttcttag tagtatgctt aaaaatttgt atattgtata    2520
tattgtaaat acatataata tataaagtta tatatttata agtaaaaaaa aaaa          2574
```

<210> SEQ ID NO 3
<211> LENGTH: 17
<212> TYPE: DNA
<213> ORGANISM: Artificial Sequence
<220> FEATURE:
<223> OTHER INFORMATION: Probe/primer derived from Mus musculus.

<400> SEQUENCE: 3
ttagcatcat gaacaac                                                   17

<210> SEQ ID NO 4
<211> LENGTH: 21
<212> TYPE: DNA
<213> ORGANISM: Artificial Sequence
<220> FEATURE:
<223> OTHER INFORMATION: Probe/primer derived from Mus musculus.

<400> SEQUENCE: 4
ccttaccctc atagtagctc a                                              21

<210> SEQ ID NO 5
<211> LENGTH: 35
<212> TYPE: DNA
<213> ORGANISM: Artificial Sequence
<220> FEATURE:
<223> OTHER INFORMATION: Probe/primer derived from Mus musculus.

-continued

```
<400> SEQUENCE: 5
gactcgagtc gacatcgatt ttttttttttt ttttt                                    35

<210> SEQ ID NO 6
<211> LENGTH: 20
<212> TYPE: DNA
<213> ORGANISM: Artificial Sequence
<220> FEATURE:
<223> OTHER INFORMATION: Probe/primer derived from Mus musculus.

<400> SEQUENCE: 6
tcaacactat cctagaagag                                                      20

<210> SEQ ID NO 7
<211> LENGTH: 17
<212> TYPE: DNA
<213> ORGANISM: Artificial Sequence
<220> FEATURE:
<223> OTHER INFORMATION: Probe/primer derived from Mus musculus.

<400> SEQUENCE: 7
gactcgagtc gacatcg                                                         17

<210> SEQ ID NO 8
<211> LENGTH: 25
<212> TYPE: DNA
<213> ORGANISM: Artificial Sequence
<220> FEATURE:
<223> OTHER INFORMATION: Probe/primer derived from Mus musculus.

<400> SEQUENCE: 8
gcagtttgga cgtcgctctg tcttg                                                25
```